United States Patent
Bateman

(10) Patent No.: US 9,750,911 B2
(45) Date of Patent: Sep. 5, 2017

(54) TRACHEOSTOMY TUBE ASSEMBLIES

(75) Inventor: Timothy Bateman, Dymchurch (GB)

(73) Assignee: Smiths Group PLC, London (GB)

( * ) Notice: Subject to any disclaimer, the term of this patent is extended or adjusted under 35 U.S.C. 154(b) by 1697 days.

(21) Appl. No.: 11/886,587

(22) PCT Filed: Mar. 6, 2006

(86) PCT No.: PCT/GB2006/000803
§ 371 (c)(1),
(2), (4) Date: Sep. 18, 2007

(87) PCT Pub. No.: WO2006/100426
PCT Pub. Date: Sep. 28, 2006

(65) Prior Publication Data
US 2009/0229614 A1 Sep. 17, 2009

(30) Foreign Application Priority Data

Mar. 19, 2005 (GB) .................... 0505729.4

(51) Int. Cl.
A61M 16/04 (2006.01)

(52) U.S. Cl.
CPC .... *A61M 16/0465* (2013.01); *A61M 16/0472* (2013.01); *A61M 16/0434* (2013.01); *A61M 16/0488* (2013.01)

(58) Field of Classification Search
CPC .............. A61M 16/04; A61M 16/0461; A61M 16/0463; A61M 16/0465
USPC ............ 128/200.24, 200.26, 207.14–207.17, 128/207.29
See application file for complete search history.

(56) References Cited

U.S. PATENT DOCUMENTS

| | | | | |
|---|---|---|---|---|
| 2,786,469 A | * | 3/1957 | Cohen ....................... | 128/200.26 |
| 2,991,787 A | * | 7/1961 | Shelden et al. .......... | 128/207.17 |
| 4,315,505 A | | 2/1982 | Crandall et al. | |
| 4,502,482 A | * | 3/1985 | DeLuccia et al. ....... | 128/207.15 |
| 4,913,139 A | | 4/1990 | Ballew | |
| 5,188,100 A | * | 2/1993 | Miles et al. ............. | 128/207.14 |
| 5,217,005 A | | 6/1993 | Weinstein et al. | |
| 5,251,616 A | * | 10/1993 | Desch ....................... | 128/200.26 |
| 5,275,611 A | * | 1/1994 | Behl ............................ | 606/198 |
| 5,443,064 A | | 8/1995 | Theis et al. | |
| 5,626,132 A | * | 5/1997 | Miller et al. ............. | 128/207.14 |
| 5,749,357 A | * | 5/1998 | Linder ..................... | 128/200.26 |

(Continued)

FOREIGN PATENT DOCUMENTS

| | | |
|---|---|---|
| EP | 0407663 | 1/1991 |
| EP | 1092448 | 4/2001 |
| EP | 1281414 | 2/2003 |

*Primary Examiner* — LaToya M Louis
(74) *Attorney, Agent, or Firm* — Louis Woo

(57) ABSTRACT

A tracheostomy tube assembly includes a flexible tube (1, 1') and a flexible introducer (2, 2') within the tube, the introducer having a passage (22) along its length for receiving a guidewire (9) inserted into the trachea (7) through a tracheostomy (6). The tube (1) has an inwardly-projecting collar (17, 17') at its patient end (11), which engages an outwardly-projecting shoulder (24, 24') on the introducer (2, 2') so that the tube does not ride rearwardly along the introducer during insertion. The flexibility of the assembly is such that it can be inserted through the tracheostomy (6) while straight and then curves to follow the guidewire (9) as its patient end enters the trachea (7).

14 Claims, 2 Drawing Sheets

(56) References Cited

U.S. PATENT DOCUMENTS

| | | | |
|---|---|---|---|
| 6,286,509 B1* | 9/2001 | Nash et al. | 128/207.14 |
| 6,722,367 B1* | 4/2004 | Blom | 128/207.14 |
| 2004/0154623 A1* | 8/2004 | Schaeffer et al. | 128/207.14 |
| 2005/0166924 A1* | 8/2005 | Thomas et al. | 128/207.14 |

* cited by examiner

TRACHEOSTOMY TUBE ASSEMBLIES

BACKGROUND OF INVENTION

This invention relates to tracheostomy tube assemblies of the kind including an outer, tubular shaft having a bore extending along it for passage of gas and an introducer inserted within the shaft, the assembly having a passage extending along its length for receiving an elongate guide member.

Tracheostomy tubes have a curved or bent shaft shaped to extend through a surgically-made opening through the neck of a patient into the trachea. An introducer within the tube is used during insertion through the neck tissue to provide a tapered tip to the assembly. One end of the tube extends externally and usually has a flange used to secure the tube with the patient's neck. The other end of the tube locates within the trachea and is directed caudally. The tube often has a cuff adjacent the patient end, which can be inflated to seal with the trachea so that flow of gas is confined along the tube. It can be difficult to insert a conventional, curved tracheostomy tube in morbidly obese patients because they may have increased neck mass such that the distance between the skin surface and the trachea is significantly greater than in average patients. One way of alleviating this problem is to use a tube with an adjustable flange, such as described in U.S. Pat. No. 5,443,064, U.S. Pat. No. 5,251,616, U.S. Pat. No. 4,235,229, U.S. Pat. No. 3,973,569 and U.S. Pat. No. 5,026,352. These arrangements enable the position of the flange along the machine end of the tube to be adjusted to take into account variations in thickness of neck tissue so that the flange can abut the surface of the skin around the tracheostomy.

It is an object of the present invention to provide an alternative tracheostomy tube assembly.

BRIEF SUMMARY OF INVENTION

According to the present invention there is provided a tracheostomy tube assembly of the above-specified kind, characterised in that the shaft and introducer are both flexible such that the assembly is adapted to bend along the trachea to follow the path of the guide member during insertion, and that the patient end of the shaft and introducer have cooperating surface formations adapted to prevent rearward displacement of the shaft along the introducer and to enable the introducer to be removed rearwardly from the shaft when the patient end of the shaft is located in the trachea.

The flexibility of the shaft is preferably such that it cannot support its own weight when supported at one end. The surface formations may include a collar projecting inwardly on the shaft and a shoulder projecting outwardly on the introducer. The surface formations may be tapered with mating tapers. The passage for receiving the guide member is preferably a passage along the introducer. The assembly may include a neck flange mounted on and movable along the shaft. The assembly may include a guide member extending along the assembly. The guide member preferably has an outer straight section and an inner curved section, the sheath and introducer being initially mounted on the straight section of the guide member and bending to follow the curve of the guide member as they are slid to a curved part of the guide member.

BRIEF DESCRIPTION OF DRAWINGS

A tracheostomy tube assembly according to the present invention will now be described, by way of example, with reference to the accompanying drawings, in which.

DETAILED DESCRIPTION OF INVENTION

Figure 1:
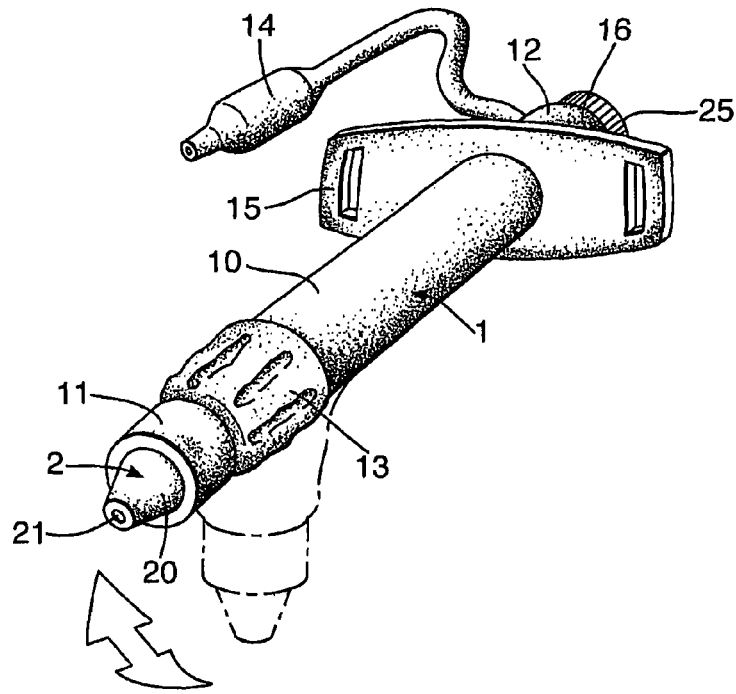
FIG. 1 is a perspective view of the assembly.
Figure 2:
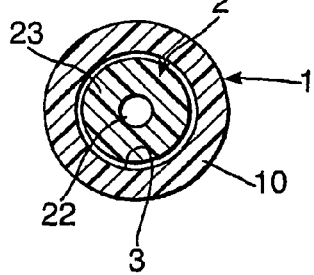
FIG. 2 is a transverse cross-sectional view of the assembly.

With reference first to FIGS. 1 to 3A, the assembly comprises an outer tube 1 and an introducer 2 extending along the bore 3 of the tube.

The tube 1 has a tubular shaft 10 of circular section and made of a soft, flexible plastics material. The flexibility of the shaft 10 is such that it cannot support its own weight when supported at one end so that, for example, its patient end 11 bends down under its own weight when the shaft is held at the machine end 12. The shaft 10 could be reinforced against radial forces by a helical wire or other reinforcement element within the wall of the shaft. The patient end 11 is square and rounded to provide a smooth tip to the tube. A sealing cuff 13 is attached to the outside of the shaft 10 in the usual way, just rearwardly of the patient end 11, the cuff being inflatable via an inflation line and connector 14. Towards its machine end 12, the tube has a flange 15 by which the tube can be secured in position about the patient's neck 4 using a tape (not shown) or the like. The flange 15 is not fixed with the shaft 10 but is slidable along it so that its position can be adjusted as desired. The flange 15 is lockable in the desired position by some locking arrangement (not shown). The locking arrangement could be of any conventional kind such as described, for example, in U.S. Pat. No. 5,443,064, U.S. Pat. No. 5,251,616, U.S. Pat. No. 4,235,229, U.S. Pat. No. 3,973,569 or U.S. Pat. No. 5,026,352. At its rear, machine end 12 the tube 1 has a conventional coupling 16, which can be left open or connected to a ventilation circuit, as necessary.

Figure 3A:
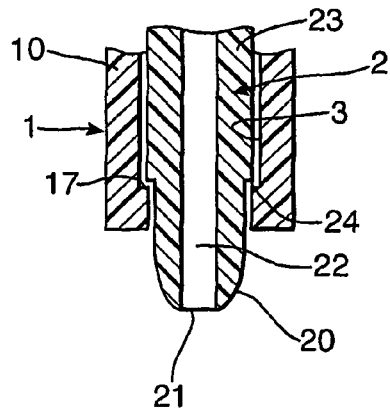
FIG. 3A is a cross-sectional side elevation view of the patient end of the assembly.
Figure 3B:
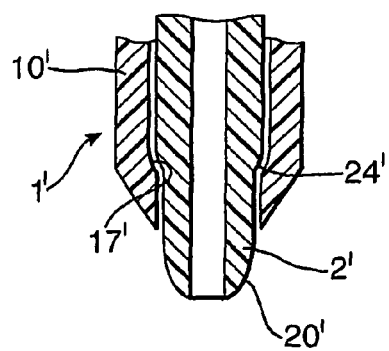
FIG. 3B is a cross-sectional side elevation view of the patient end of a modified assembly.

The introducer 2 takes the form of an elongate moulding of a soft, flexible plastics material. The patient end 20 of the introducer 2 is tapered and has a central opening 21 at its tip from a passage 22 extending along its length. Just to the rear of the tapered end 20, the introducer 2 is formed with a surface formation in the form of a radially outwardly projecting annular shoulder 24. This engages a radially inwardly projecting collar 17 formed around the patient end 11 of the shaft 10 with the tapered end 20 of the introducer 2 projecting beyond the patient end of the tube 1 to provide a tapering nose to the assembly and to form a substantially smooth transition with the external surface of the shaft. FIG. 3B shows a modified form of the assembly where equivalent components have been given the same reference numeral with the addition of a prime '. In this arrangement, it can be seen that the shoulder 24' and the collar 17' both have tapering surfaces that mate with one another.

The main body 23 of the introducer 2 has a circular section, as shown. At its rear, machine end 25, the introducer 2 projects a short distance from the machine end 12 of the tube 1.

The combined assembly of the tube 1 and introducer 2 is highly flexible, enabling the patient end of the assembly to be readily bent. The soft flexible nature of the shaft 10 makes it susceptible to being compressed axially but the engagement of the collar 17 on the tube 1 with the shoulder 13 on the introducer 2 prevents the tube riding rearwardly along the introducer during insertion.

Figure 4:
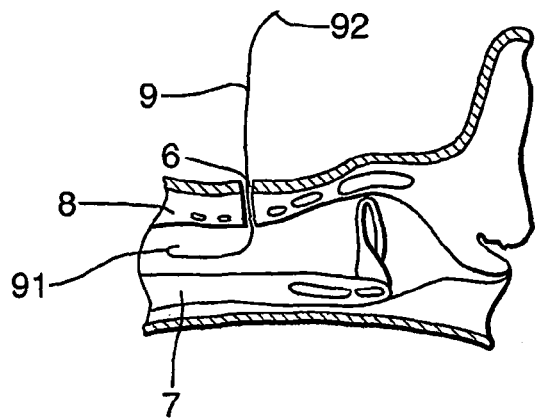
FIGS. 4 to 6 show successive stages in insertion of the assembly.

The method of using the assembly will now be described with reference to FIGS. 4 to 6. An opening 6 is first made into the trachea 7 through neck tissue 8 in any conventional manner and a guidewire 9, or other bendable elongate member, is placed to extend through the opening with its patient end 91 located in the trachea and its machine end 92 located externally, as shown in FIG. 4. It can be seen that the outer part of the guidewire is substantially straight and the inner part of the guidewire is curved. The machine end 92 of the guidewire 9 is threaded through the opening 21 to the passage 22 through the introducer 2. The main body of the introducer need not be of circular shape, as described above, instead it may take the form of a rectangular-section strip similar to that described in U.S. Pat. No. 5,222,487 or U.S. Pat. No. 5,042,475 but having greater flexibility. With such a strip introducer, the gap between the introducer and the inside of the tube shaft would provide the passage for the guide wire.

Figure 5:
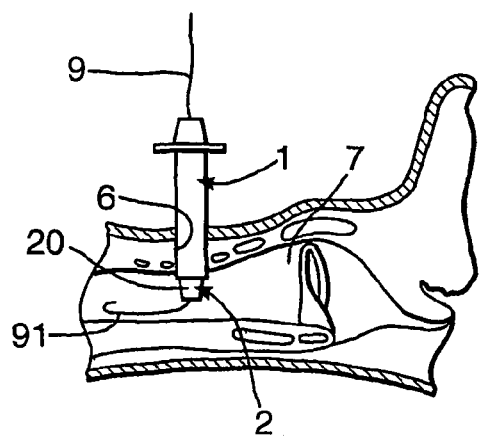
Figure 6:
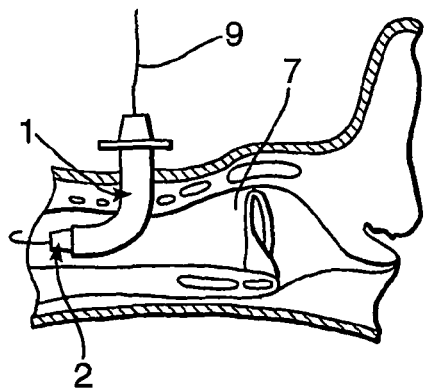

The patient end of the assembly of the tube 1 and introducer 2 is slid along the guidewire 9 through the opening 6 until the patient end locates in the trachea 7, as shown in FIG. 5. During insertion of the assembly through the neck tissue 8 the user maintains the assembly in a straight shape so that axial force can be applied to its patient end. As the assembly is pushed in further, its highly flexible nature is such that its patient end is guided caudally down the trachea 7 by the guidewire 9, as shown in FIG. 6. When the assembly has been inserted to the desired extent, the introducer 2 is pulled out rearwardly and the flange 15 is moved forward to abut the surface of the neck 4 and is then locked in position. The bore 3 along the tube 1 provides a gas passage into the trachea 7.

The assembly is particularly useful in obese or other patients with excessive thickness of neck tissue since it enables a tracheostomy tube to be correctly placed within the trachea with a low risk of trauma to the posterior wall of the trachea. The assembly enables one size, or a small range of sizes, to be stocked for use with patients having a wide range of different anatomies.

The tube could be steerable in order to facilitate following the guide wire. This could be achieved by means of a pull cord extending within a lumen along the wall of the tube and attached close to the patient of the tube on the inside of the desired curve so that, by pulling on the cord, the tip of the tube bends.

The invention claimed is:

1. A tracheostomy tube assembly comprising:
    an outer, tubular shaft having a bore extending along the shaft for passage of gas, a distal end, and a radially inwardly projecting collar at an inner circumferential wall of the shaft; and
    an introducer inserted within the shaft to provide a tapered tip to the assembly adapted to be used to introduce the assembly through tracheal tissue of a patient during insertion of the assembly into the trachea of the patient, the introducer having a distal portion that is adapted to extend beyond the distal end of the shaft, the distal portion of the introducer being tapered towards a distal opening of a passage extending along the length of the introducer adapted to receive an elongate guide member, the introducer further having an annular shoulder projecting outwardly from its outer circumferential wall;
    wherein when the introducer is fully inserted into the shaft, the tapered distal portion of the introducer extends beyond the distal end of the shaft to provide a projecting, tapering nose that forms the tapered tip for the assembly for introducing and guiding the assembly through the tracheal tissue during insertion to the trachea;
    wherein one end of the elongate guide member is threaded through the distal opening of the introducer to the passage through the introducer so that the introducer is guided by and can slide along the elongate guide member, and another end of the elongate member is adapted to be located through an opening at the neck of the patient into the trachea of the patient;
    wherein the radially projecting collar at the shaft and the annular shoulder at the introducer are engaged with each other to prevent rearward displacement of the shaft along the introducer as first the tapered distal portion of the introducer and then the shaft are guided by the elongate guide member into the trachea of the patient; and
    wherein after the shaft is properly located in the trachea of the patient, the introducer is removed rearwardly from the shaft so that the bore of the shaft is free to provide a gas passage to the trachea.

2. A tracheostomy tube assembly of claim 1, wherein the shaft and the introducer are both flexible such that the assembly is adapted to follow a bend of the elongate guide member after the elongate guide member is inserted into the trachea of a patient.

3. A tracheostomy tube assembly of claim 1, wherein the tapered distal portion of the introducer forms a substantially smooth transition with an external surface of the shaft.

4. A tracheostomy tube assembly according to claim 1, wherein flexibility of the shaft is such that it cannot support its own weight when supported at one end.

5. A tracheostomy tube assembly according to claim 1, wherein the radially projecting collar at the shaft and the annular shoulder at the introducer have respective surface formations with mating tapers.

6. A tracheostomy tube assembly according to claim 1, further comprising a neck flange mounted on and movable along the shaft.

7. A tracheostomy tube assembly according to claim 1, wherein the elongate guide member has an outer straight section and an inner curved section;
    wherein the shaft and introducer are initially mounted on the straight section of the guide member and bend to follow the curve of the guide member as they are slid to a curved part of the guide member.

8. A tracheostomy tube assembly comprising a shaft having a distal end and a bore extending along the shaft, an introducer matingly fitted into the bore with a tapered distal portion extending beyond the distal end of the shaft toward a distal opening at the introducer that opens into a passage that extends along the length of the introducer, the opening dimensioned to allow one end of an elongate member to be threaded therethrough into the passage so that the introducer can guidedly slide along the elongate member, the tapered distal portion of the introducer including a tapering nose adapted to act as a tip for the assembly to assist in introducing the assembly though tracheal tissue of a patient and the inserting of the shaft into the trachea of the patient after another end of the elongate guide member is inserted into the trachea of the patient, a radially inwardly projecting collar at the shaft and an outwardly projecting annular shoulder at the introducer engage to each other to cause the shaft to follow movement of the introducer when the assembly is being guided by the elongate member into the trachea of the patient, the introducer being removable rearwardly from the shaft so that the bore of the shaft is opened to provide a gas passage to the trachea after the shaft is properly located in the trachea of the patient.

9. A tracheostomy tube assembly of claim 8, wherein the shaft and the introducer are both flexible such that the assembly is adapted to follow a bend of the elongate guide member in the trachea of the patient as the assembly is inserted into the trachea of a patient.

10. A tracheostomy tube assembly of claim 8, wherein the tapered distal portion of the introducer forms a substantially smooth transition with an external surface of the shaft.

11. A tracheostomy tube assembly according to claim 8, wherein flexibility of the shaft is such that it cannot support its own weight when supported at one end.

12. A tracheostomy tube assembly according to claim 8, wherein the radially projecting collar at the shaft and the annular shoulder at the introducer have respective surface formations with mating tapers.

13. A tracheostomy tube assembly according to claim 8, further comprising a neck flange mounted on and movable along the shaft.

14. A tracheostomy tube assembly according to claim 8, wherein the elongate guide member has an outer straight section and an inner curved section;
   wherein the shaft and introducer are initially mounted on the straight section of the guide member and bend to follow the curve of the guide member as they are slid to a curved part of the guide member.

* * * * *